United States Patent
Araujo

(10) Patent No.: US 8,000,803 B2
(45) Date of Patent: Aug. 16, 2011

(54) IMPLANTABLE LEAD ATTACHMENT

(75) Inventor: Alfredo Araujo, Sylmar, CA (US)

(73) Assignee: Alfred E. Mann Foundation For Scientific Research, Santa Clarita, CA (US)

(*) Notice: Subject to any disclaimer, the term of this patent is extended or adjusted under 35 U.S.C. 154(b) by 1135 days.

(21) Appl. No.: 11/278,941

(22) Filed: Apr. 6, 2006

(65) Prior Publication Data

US 2007/0034675 A1 Feb. 15, 2007

Related U.S. Application Data

(60) Provisional application No. 60/694,011, filed on Jun. 25, 2005.

(51) Int. Cl.
*A61N 1/04* (2006.01)
*H01R 4/10* (2006.01)

(52) U.S. Cl. .................. 607/116; 439/909; 439/877

(58) Field of Classification Search .............. 439/877, 439/879, 909; 607/115, 116, 37, 117–132; 604/37, 9, 36; 606/129, 151, 215
See application file for complete search history.

(56) References Cited

U.S. PATENT DOCUMENTS

| | | | | |
|---|---|---|---|---|
| 3,717,842 | A * | 2/1973 | Douglas, Jr. | 174/84 R |
| 3,732,528 | A * | 5/1973 | Vetter | 439/879 |
| 3,955,044 | A * | 5/1976 | Hoffman et al. | 439/730 |
| 5,746,616 | A * | 5/1998 | Mar | 439/245 |
| 6,289,251 | B1 * | 9/2001 | Huepenbecker et al. | 607/116 |
| 6,951,491 | B2 * | 10/2005 | Sakaguchi et al. | 439/879 |
| 7,027,852 | B2 * | 4/2006 | Helland | 607/127 |
| 7,435,257 | B2 * | 10/2008 | Lashinski et al. | 623/2.11 |
| 7,856,277 | B1 * | 12/2010 | Thacker et al. | 607/117 |
| 2002/0193859 | A1 * | 12/2002 | Schulman et al. | 607/116 |
| 2003/0220676 | A1 * | 11/2003 | Helland | 607/122 |
| 2005/0234318 | A1 * | 10/2005 | Schulman et al. | 600/373 |
| 2006/0111767 | A1 * | 5/2006 | Olson et al. | 607/116 |
| 2006/0136025 | A1 * | 6/2006 | Webler | 607/120 |
| 2008/0015580 | A1 * | 1/2008 | Chao | 606/61 |
| 2008/0125637 | A1 * | 5/2008 | Geist et al. | 606/301 |

* cited by examiner

*Primary Examiner* — Briggitte R Hammond
(74) *Attorney, Agent, or Firm* — Gary D. Schnittgrund

(57) ABSTRACT

The invention is a lead attachment suitable for implantation in living tissue that enables connection of a wire that is comprised of stainless steel to a tack that in turn is bonded to a titanium swage cup, preferably Ti-6Al-4V. The wire is attached by crimping inside a crimping tube, to assure electrical continuity from the wire to the crimping tube. The tack is bonded by swaging a thinned swage ring and is further sealed by welding to swage cup, which is bonded by brazing to ceramic case.

12 Claims, 1 Drawing Sheet

IMPLANTABLE LEAD ATTACHMENT

CROSS REFERENCE TO RELATED APPLICATION

This application claims the benefit of U.S. Provisional Application Ser. No. 60/694,011, filed on Jun. 25, 2005.

FIELD OF THE INVENTION

This invention relates to a prosthetic medical device and method, and more particularly to connecting electrically conducting wires to a miniature implantable device to minimize risk to the living tissue during and after surgery.

BACKGROUND OF THE INVENTION

Neurological disorders are often caused by neural impulses failing to reach their natural destination in otherwise functional body systems. Local nerves and muscles may function, but, for various reasons, such as injury, stroke, or other cause, the stimulating nerve signals do not reach their natural destination. For example, paraplegic and quadriplegic animals have intact nerves connected to functioning muscles and only lack the brain-to-nerve link. Electrically stimulating the nerve or muscle can provide a useful muscle contraction.

Further, implanted devices may be sensors as well as stimulators. In either case, difficulties arise both in providing suitable, operable stimulators or sensors which are small in size and in passing sufficient energy and control information to or from the device, with or without direct connection, to satisfactorily operate them. Miniature monitoring and/or stimulating devices for implantation in a living body are disclosed by Schulman, et al. (U.S. Pat. No. 6,164,284), Schulman, et al. (U.S. Pat. No. 6,185,452), and Schulman, et al. (U.S. Pat. No. 6,208,894), each of which is incorporated by reference in its entirety.

It must be assured that the electrical current flow does not damage the intermediate body cells or cause undesired stimulation. Anodic or cathodic deterioration of the stimulating electrodes must not occur.

At least one small stimulator or sensor disposed at various locations within the body may send or receive signals via electrical wires. The implanted unit must be sealed to protect the internal components from the body's aggressive environment. If wires are attached to the stimulator, then these wires and the area of attachment must be electrically insulated to prevent undesired electric signals from passing to surrounding tissue.

Miniature stimulators offer the benefit of being locatable at a site within the body where a larger stimulator cannot be placed because of its size. The miniature stimulator may be placed into the body by injection. The miniature stimulator offers other improvements over larger stimulators in that they may be placed in the body with little or no negative cosmetic effect. There may be locations where these miniature devices cannot be fitted to achieve the desired sending or receiving of signals. Such locations include, but are not limited to, the tip of a finger for detection of a stimulating signal or near an eyelid for stimulating blinking. In such locations, the stimulator and its associated electronics are preferably located at a distance removed from the sensing or stimulating site within the body; thus creating the need to carry electrical signals from the detection or stimulation site to the remote miniature stimulator, where the signal wire must be securely fastened to the stimulator.

Further, the miniature stimulator may contain a power supply that requires periodic charging or require replacement, such as a battery. When this is the case, the actual stimulation or detection site may be located remotely from the stimulator and may be located within the body, but removed a significant distance from the skin surface. By having the ability to locate the miniature stimulator near the skin while the stimulation site is at some distance removed from the skin, the miniature stimulator and its associated electronics can be more effectively replaced by a surgical technique or more efficiently recharged through the skin by any of several known techniques, including the use of alternating magnetic fields. If the electronics package is replaced surgically, then it is highly desirable to have the capability to reconnect the lead wires to the miniature stimulator via an easy, rapid and reliable method, as disclosed herein.

There is a need for an improved attachment system for implantable wires, which may be dissimilar materials that cannot be joined to each other by welding.

SUMMARY OF THE INVENTION

A lead attachment adapted to join dissimilar metal conductors that cannot be joined by welding comprising a tack and a swage cup that is adapted to receive the tack; the swage cup further comprising a swage ring having a relief area that retains the tack by bending the relief area over the tack. A swage ring contains the relief area, the relief area having a wall thickness that is between about 0.005 and 0.006 inches thick. The tack is comprised of stainless steel and the swage cup is comprised of titanium or an alloy of titanium. The tack is welded to the swage cup. The swage cup has a centering ring to center a case for bonding thereto. The swage cup comprises a centering cup to center a case for bonding thereto. The tack has a crimping tube for bonding to an electrical conductor.

The novel features of the invention are set forth with particularity in the appended claims. The invention will be best understood from the following description when read in conjunction with the accompanying drawings.

DETAILED DESCRIPTION OF THE PREFERRED EMBODIMENT

Figure 1:
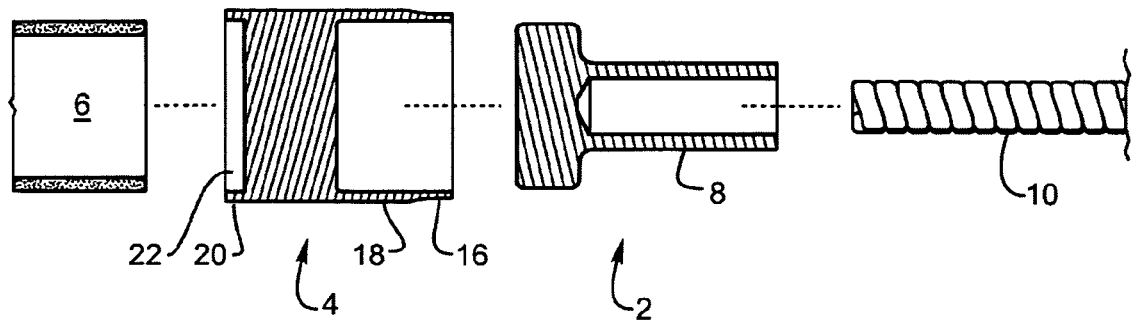
FIG. 1 illustrates a cross-sectional view of the tack and swage cup.

FIG. 1 provides a cross-sectional view of a preferred embodiment of the implantable electrically conductive lead attachment. This device enables electrical connection to be achieved between conductors of dissimilar materials that cannot be joined by welding, which is especially beneficial for implantable devices, such as miniature monitoring and/or stimulating devices for implantation in living tissue as disclosed by Schulman, et al. (U.S. Pat. No. 6,164,284), Schulman, et al. (U.S. Pat. No. 6,185,452), and Schulman, et al. (U.S. Pat. No. 6,208,894), all of which are incorporated herein by reference in their entirety.

Figure 2:
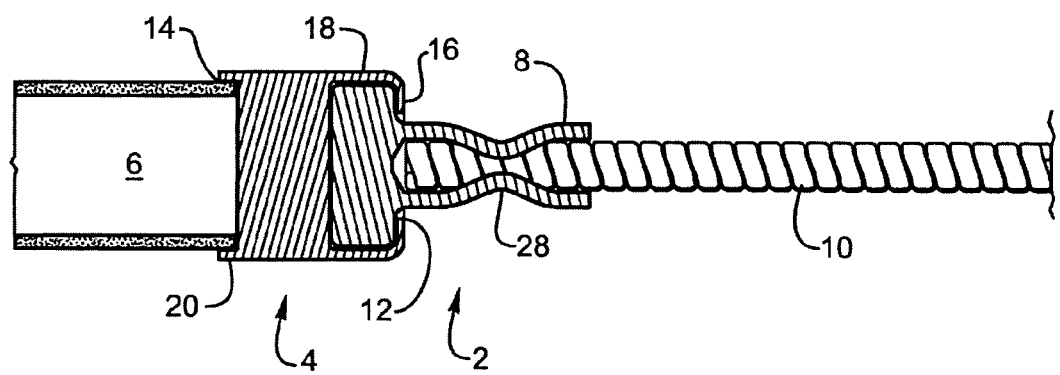
FIG. 2 illustrates a cross-sectional view of the tack and swage cup assembly showing a wire and case.

The tack 2 is preferably comprised of stainless steel, such as 316-stainless steel. In a preferred embodiment, the material selection that comprises tack 2 is the same as the material that comprises an electrical conductor, such as wire 10, FIG. 2. Tack 2 is slideably placed in swage cup 4, surrounded by integral swage ring 18, which in a preferred embodiment has a wall thickness of about 0.007 inches. Swage cup 4 is preferably comprised of a biocompatible, electrically conductive metal such as a titanium alloy, for example Ti-6Al-4V.

The swage ring 18 and relief area 16, which in a preferred embodiment has a wall thickness of about 0.005 to 0.006 inches, is mechanically turned or swaged over the tack 2 at room temperature, thereby retaining tack 2 in swage cup 4. A weld joint 12 is formed to seal the tack 2 in the swage cup 4 and to eliminate fluid leakage from the surrounding milieu into the space between the two components.

The wire 10 is electrically conductive and is about 0.032 inches in diameter. It is preferably comprised of stainless steel, for example 316-stainless steel. It may be used to conduct electrical signals to or from locations remote from a microstimulator or microsensor that is attached to swage cup 4 at braze joint 14. The wire 10 is placed into crimping tube 8 which is then crimped to retain the wire 10 inside the tube 8 by virtue of crimp 28.

In a preferred embodiment, case 6 is comprised of a biocompatible material, such as a non-conducting ceramic selected from the group consisting of alumina, glass, titania, zirconia, stabilized-zirconia, partially-stabilized zirconia, tetragonal zirconia, magnesia-stabilized zirconia, ceria-stabilized zirconia, yttria-stabilized zirconia, or calcia-stabilized zirconia.

Figure 3:
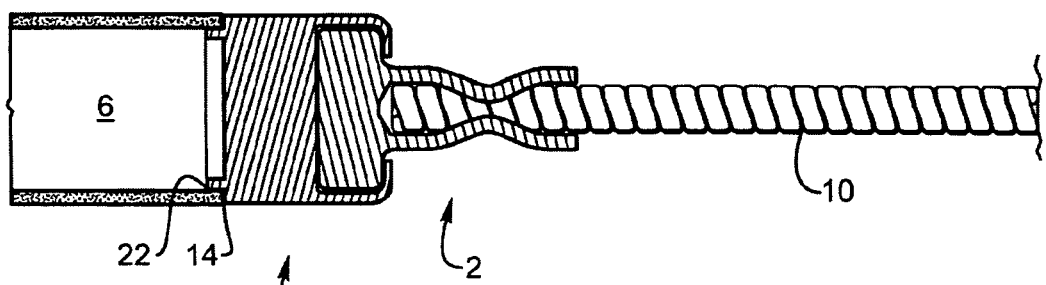
FIG. 3 illustrates a cross-sectional view of the tack and swage cup showing a centering cup for a case on the swage cup.

The case 6 contains and protects an electronic package from the environment and hermetically seals the electronics. In a preferred embodiment the case 6 is brazed to the metal end cap swage cup at braze joint 14. An integral centering ring 20 in swage cup 4 enables the case 6 to be positioned and centered in the swage cut 4 during the bonding process. An alternate embodiment, FIG. 3, utilizes a centering cup 22 that is raised to enter into the end of tube 6 for centering the tube 6.

Obviously, many modifications and variations of the present invention are possible in light of the above teachings. It is therefore to be understood that, within the scope of the appended claims, the invention may be practiced otherwise than as specifically described.

What is claimed is:

1. A living tissue surgically implantable biocompatible lead attachment adapted to join dissimilar metal conductors, comprising: a biocompatible tack adapted to be surgically implanted and a biocompatible swage cup adapted to be surgically implanted, said swage cup adapted to receive said biocompatible tack; said biocompatible swage cup further comprising a swage ring having a relief area that retains said biocompatible tack by bending said relief area over said biocompatible tack.

2. The lead attachment according to claim 1, wherein said swage ring contains said relief area, said relief area having a wall thickness that is between about 0.005 and 0.006 inches thick.

3. The lead attachment according to claim 1, wherein said tack is comprised of stainless steel.

4. The lead attachment according to claim 1, wherein said swage cup is comprised of titanium or an alloy of titanium.

5. The lead attachment according to claim 1, wherein said tack is welded to said swage cup.

6. The lead attachment according to claim 1, wherein said swage cup comprises a centering ring to center a case for bonding thereto.

7. The lead attachment according to claim 1, wherein said swage cup comprises a centering cup to center a case for bonding thereto.

8. The lead attachment according to claim 1, wherein said tack comprises a crimping tube for bonding to an electrical conductor.

9. A living tissue surgically implantable biocompatible lead attachment adapted to join dissimilar metal conductors, comprising:

a biocompatible tack adapted to be surgically implanted; a biocompatible swage cup that is adapted to receive said tack; said swage cup further comprising a swage ring having a relief area that retains said tack by bending said relief area over said tack;

a biocompatible crimping tube adapted to be surgically implanted, said biocompatible crimping tube being integral with said tack and receives an implantable electrical conductor; and a biocompatible centering ring adapted to be surgically implanted for centering a case in said swage cup.

10. The lead attachment according to claim 9, wherein said tack is comprised of stainless steel.

11. The lead attachment according to claim 9, wherein said swage ring is comprised of titanium or an alloy of titanium.

12. A method of attaching dissimilar living tissue surgically implantable biocompatible metal conductors comprising the steps of:

selecting a surgically implantable biocompatible stainless steel tack;

inserting a surgically implantable biocompatible stainless steel conductor in an implantable crimping tube of said surgically implantable biocompatible tack;

inserting said surgically implantable tack into a surgically implantable biocompatible swage cup that comprises a surgically implantable biocompatible swage cup having a relief area;

swaging said relief area to retain said surgically implantable biocompatible tack; and welding said relief area to said surgically implantable biocompatible tack.

\* \* \* \* \*